(12) United States Patent
Chen

(10) Patent No.: US 7,163,490 B2
(45) Date of Patent: Jan. 16, 2007

(54) EXERCISE MONITORING AND RECORDING DEVICE WITH GRAPHIC EXERCISE EXPENDITURE DISTRIBUTION PATTERN

(76) Inventor: Yu-Yu Chen, 2Fl., No. 349, Wushing St., Shinyi Chiu, Taipei (TW) 110

( * ) Notice: Subject to any disclaimer, the term of this patent is extended or adjusted under 35 U.S.C. 154(b) by 413 days.

(21) Appl. No.: 10/854,201

(22) Filed: May 27, 2004

(65) Prior Publication Data

US 2005/0266960 A1     Dec. 1, 2005

(51) Int. Cl.
*A63B 21/00* (2006.01)
*A63B 22/00* (2006.01)

(52) U.S. Cl. .................... 482/8; 482/1; 482/9; 482/900

(58) Field of Classification Search ................ 482/1–9, 482/900–902; 702/127, 141, 142, 160
See application file for complete search history.

(56) References Cited

U.S. PATENT DOCUMENTS 5,065,414 A * 11/1991 Endou et al. ............... 377/24.2
6,095,949 A * 8/2000 Arai .............................. 482/4
6,836,524 B1 * 12/2004 Lee ........................... 377/24.2

* cited by examiner

*Primary Examiner*—Glenn E. Richman
(74) *Attorney, Agent, or Firm*—Rosenberg, Klein & Lee

(57) ABSTRACT

An exercise monitoring and recording device includes a motion signal sensing circuit for detecting a series of motion signals of a user and a microprocessor for receiving the motion signals. The microprocessor is connected with at least one exercise expenditure distribution pattern storage for storing the motion signals and generating an exercise expenditure distribution pattern with reference to a real time signal from a real time clock generating circuit. The device includes a daily exercise expenditure distribution pattern storage for storing of daily exercise expenditure distribution pattern, a weekly exercise expenditure distribution pattern storage for storing weekly exercise expenditure distribution pattern, and a monthly exercise expenditure distribution pattern for storing monthly exercise expenditure distribution pattern.

7 Claims, 5 Drawing Sheets

EXERCISE MONITORING AND RECORDING DEVICE WITH GRAPHIC EXERCISE EXPENDITURE DISTRIBUTION PATTERN

BACKGROUND OF THE INVENTION

1. Field of the Invention

The present invention relates to an exercise monitoring device, and more particularly to an exercise monitoring and recording device capable to display exercise expenditure in the form of graphic distribution pattern.

2. Description of the Prior Art

There are variety of body building devices and exercisers developed for people who live busily in the modern commercial society and require appropriate exercises. For a person to accurately control a moderate amount of exercise and monitor personal physical condition, various types of body/motion signal sensing devices have been researched and developed.

Typically, the conventional body/motion signal sensing devices comprises a display unit for displaying the amount of exercise in digital value. Take for an example. Pedometer is a simple body/motion signal sensing device extensively used by exercisers. Pedometer is used to measure the accumulated number of paces of an exerciser at walking, jogging, or jumping, and the accumulated number of paces is displayed in digits on the display unit of the pedometer. Currently, there are a variety of pedometers available in the market, which possess different functions, such as disclosed in U.S. Pat. Nos. 4,371,945 and 5,164,967. The electronic pedometers are capable to calculate the distance a user walks, jogs or runs by electronically measuring the length of each stride taken by the user, and display the distance traveled on a digital display.

However, most of the pedometers are limited in functions. Those pedometers are only capable to display simple digital data which are limited in information and do not match the requirement of most exercisers. Hence, the exercisers are not able to know their conditions, records, and exercise expenditure. In other words, the digital data shown on the digital displays of the pedometers are not informative enough.

In most applications, data are expressed in digits and are clear to reflect the facts and changes. However, in some applications, graphical data would be more readable than digital data. Thus, it is desired to develop an exercise monitoring and recording device capable to show graphical records.

SUMMARY OF THE INVENTION

A primary object of the present invention is to provide an exercise monitoring and recording device that is capable to record the exercise expenditure of a user and display his exercise expenditure distribution in graphic pattern. Hence, the user can monitor his exercise expenditure and conditions.

Another object of the present invention is to provide an exercise monitoring and recording device which enables the user to select the types of graphic exercise expenditure distribution patterns to be displayed. The device comprises a memory that stores the graphic exercise expenditure distribution patterns of the user, and enables the user to view or to analyze his exercise records at any days, weeks or months.

To achieve the above and other objects, in accordance with the present invention, there is provided with an exercise monitoring and recording device with graphic expenditure distribution. The device comprises a motion signal sensing circuit which includes a vibration sensor for detecting a series of motion signals of a user and a microprocessor for receiving the motion signals. The microprocessor is connected with at least one exercise expenditure distribution pattern storage for storing the motion signal and generating an exercise expenditure distribution pattern in accordance with the real time from a real time clock generating circuit. The user can select the type of exercise expenditure distribution pattern to be displayed at a display unit.

In a preferred embodiment, the device includes a daily exercise expenditure distribution pattern storage for storing of daily exercise expenditure distribution pattern, a weekly exercise expenditure distribution pattern storage for storing weekly exercise expenditure distribution pattern, and a monthly exercise expenditure distribution pattern for storing monthly exercise expenditure distribution pattern.

The present invention will be apparent to those skilled in the art by reading the following description of the best mode and a preferred embodiment of a device for carrying out the present invention, with reference to the attached drawings, in which:

DETAILED DESCRIPTION OF THE PREFERRED EMBODIMENTS

Figure 1:
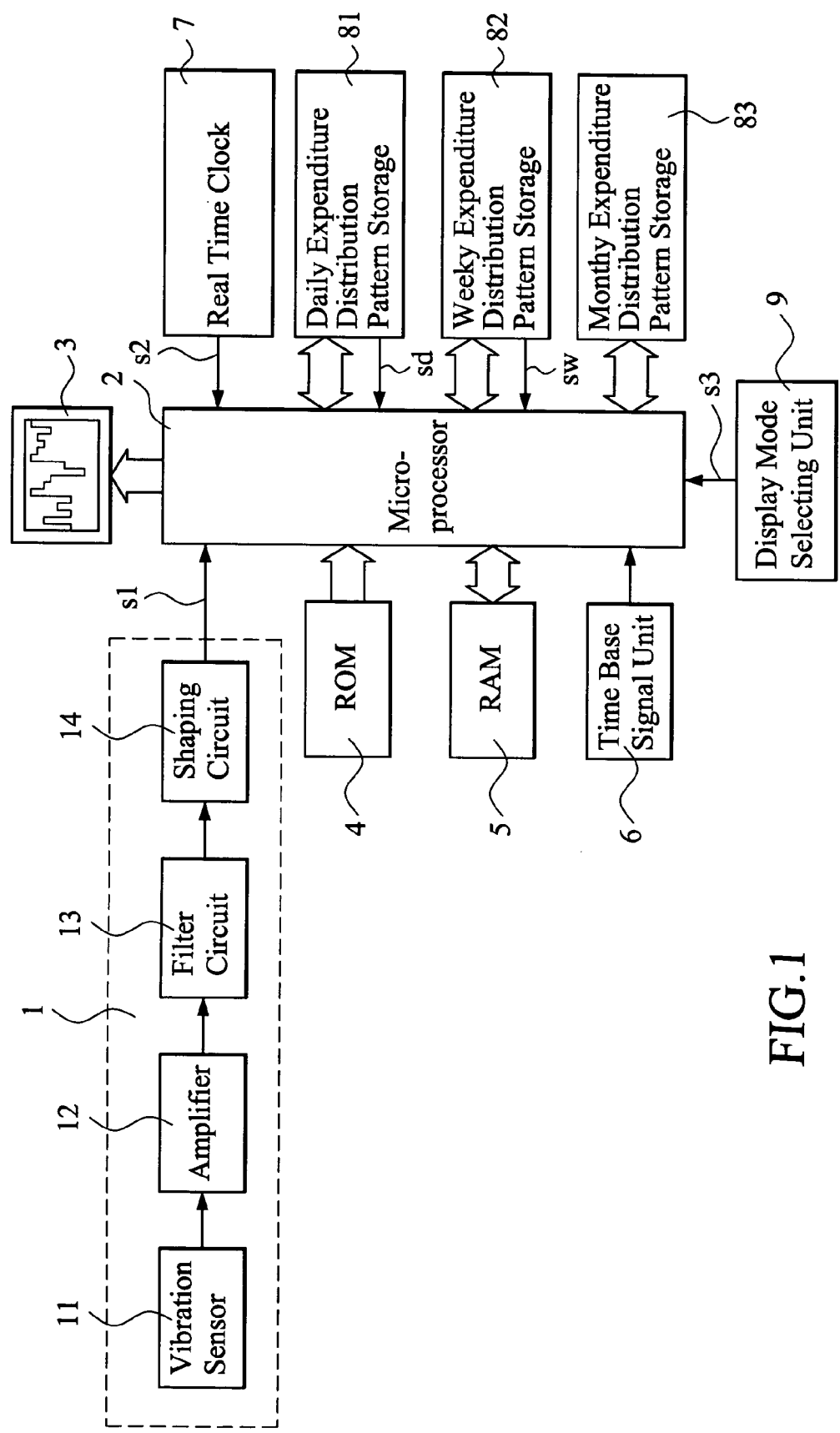
FIG. 1 is a functional block diagram of an exercise monitoring and recording device with graphic exercise expenditure distribution pattern according to the present invention.

Please refer to the drawings and in particular to FIG. 1 which is the functional block diagram of an exercise monitoring and recording device constructed in according to the present invention. The exercise monitoring and recording device comprises a motion signal sensing circuit 1 which includes a vibration sensor 11 capable to detect a series of motion signals of a user at exerciser. The vibration sensor 11 may comprise, for example, a conventional pedometer.

The motion signal detected by the vibrator sensor 11 is forwarded to an amplifier 12 for amplification. The amplified signal is then transmitted to a filter circuit 13 for filtering the noises and then to a shaping circuit 14 for shaping. Subsequently, the motion signal s1 is sent to a microprocessor 2.

The microprocessor 2 is coupled with a display unit 3 capable of displaying the graphic exercise expenditure distribution patterns of the user. Also, a read only memory (ROM) 4 and a random access memory (RAM) 5 are coupled with the microprocessor 2 for separately storing the control program for controlling the operation of the exercise monitoring and recording device and the temporary data generated at operation of program.

The microprocessor 2 is also connected with a time base signal unit 6 which provides a time base signal s2 to the microprocessor 2. A real time clock generating circuit 7 is connected with the microprocessor 2 for providing a real time signal s2 to the microprocessor 2.

Moreover, the exercise monitoring and recording device comprises at least one storage unit for storing the motion signals. An exercise expenditure distribution pattern is generated from the motion signals s2 detected by the motion signal sensing circuit 1 and the real time of the real time clock generating circuit 7.

In a preferred embodiment, the storage unit comprises a daily exercise expenditure distribution pattern storage 81, a weekly exercise expenditure distribution pattern storage 82 and a monthly exercise expenditure distribution pattern storage 83.

The daily exercise expenditure distribution pattern storage 81 stores the exercise expenditure distribution pattern of the user of a day. In the case the daily exercise expenditure distribution pattern storage 81 contains data for over 24 hours, the daily exercise expenditure distribution pattern storage 81 sends a carry signal sd to the microprocessor 2. Then, the microprocessor 2 will transfer the exercise expenditure distribution pattern of the first day of the daily exercise expenditure distribution pattern to the weekly exercise expenditure distribution pattern storage 82, which will become the first day pattern of the weekly exercise expenditure distribution pattern.

The weekly exercise expenditure distribution pattern storage 82 stores the exercise expenditure distribution pattern of the user of a week. Similarly, when the weekly exercise expenditure distribution pattern storage 82 contains data for over 7 days, the weekly exercise expenditure distribution pattern storage 82 sends a carry signal sw to the microprocessor 2. Then, the microprocessor 2 will transfer the exercise expenditure distribution pattern of the first week of the weekly exercise expenditure distribution pattern to the monthly exercise expenditure distribution pattern storage 83, which will constitute the first week pattern of the monthly exercise expenditure distribution pattern.

Figure 2:
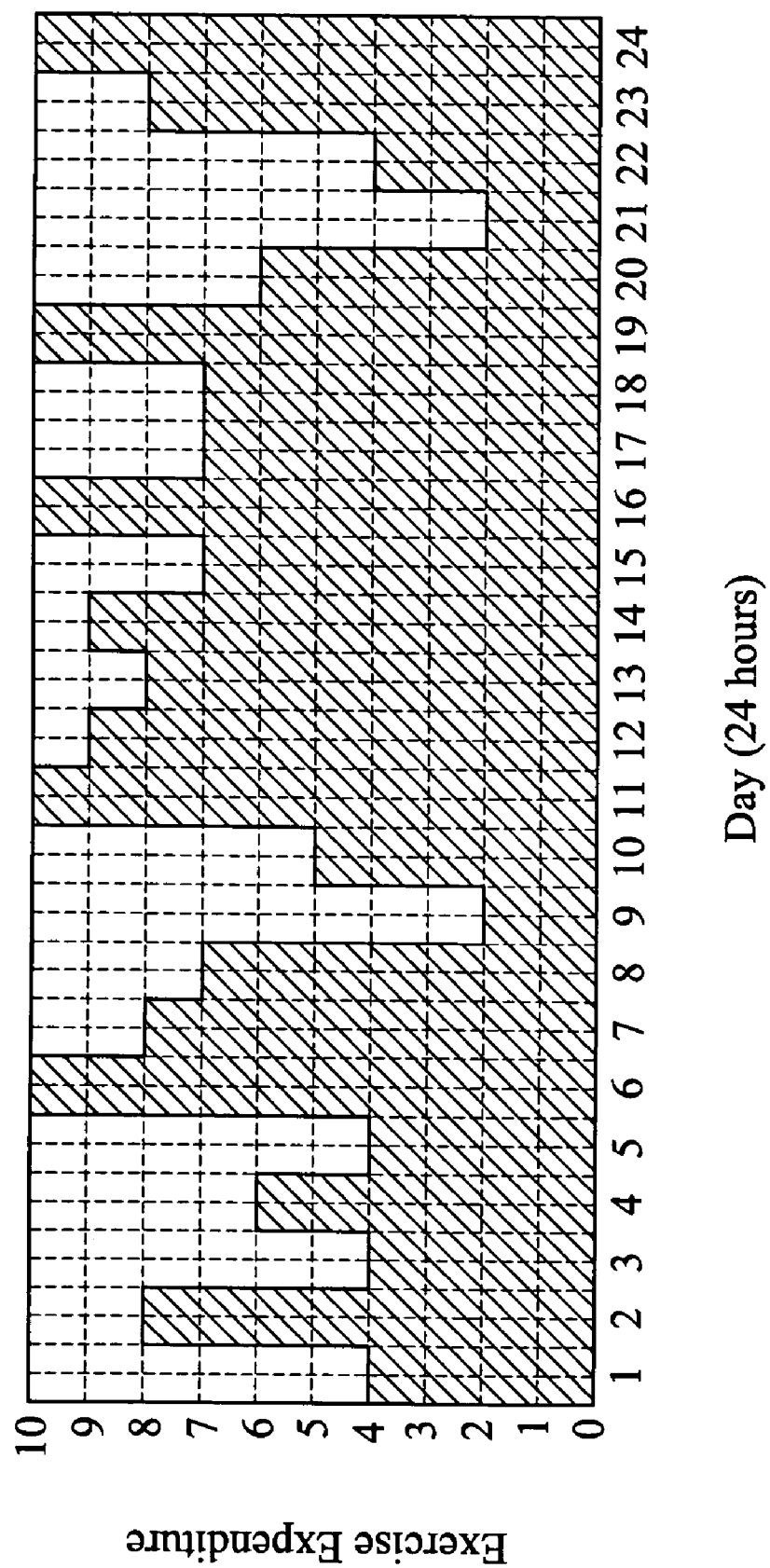
FIG. 2 shows a daily graphic exercise expenditure distribution pattern of a user recorded by the device.

Please refer to FIG. 2, which shows a daily graphic exercise expenditure distribution pattern of the user. Basically, the unit of the X-axis of the daily exercise expenditure distribution pattern is hour. The exercise expenditure of the user, which includes, for example, accumulated number of pace, accumulated distance of walking, or calorie consumed at every hour of that day is recorded and plotted against time, forming the daily exercise expenditure distribution pattern.

Figure 3:
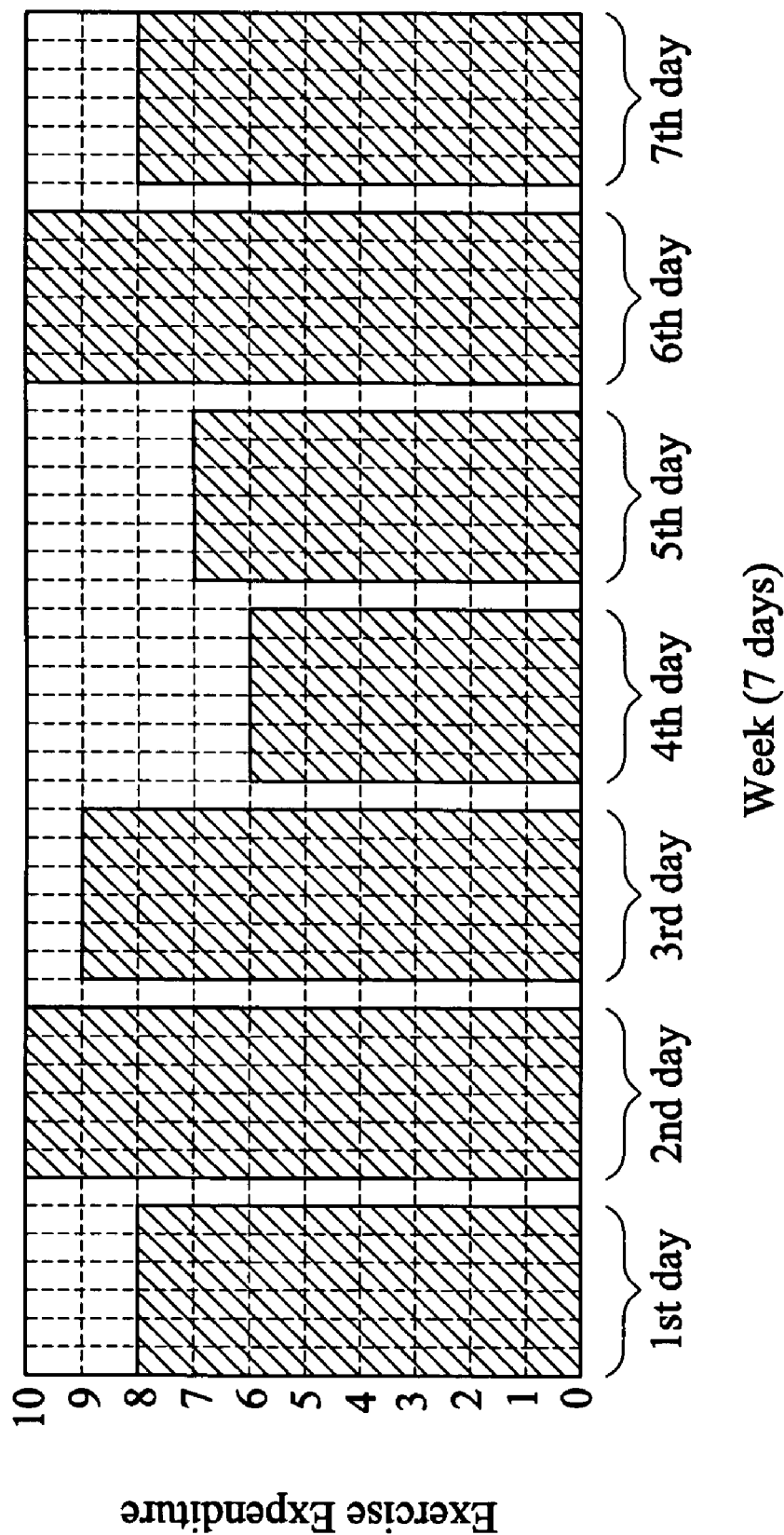
FIG. 3 shows the weekly graphic exercise expenditure distribution pattern of the user recorded by the device.

FIG. 3 shows the weekly graphic exercise expenditure distribution pattern of the user recorded by the device. The unit of the X-axis of the weekly exercise expenditure distribution pattern is day. The weekly exercise expenditure distribution pattern storage 82 stores the exercise expenditure that the user is taken in 7 days.

Figure 4:
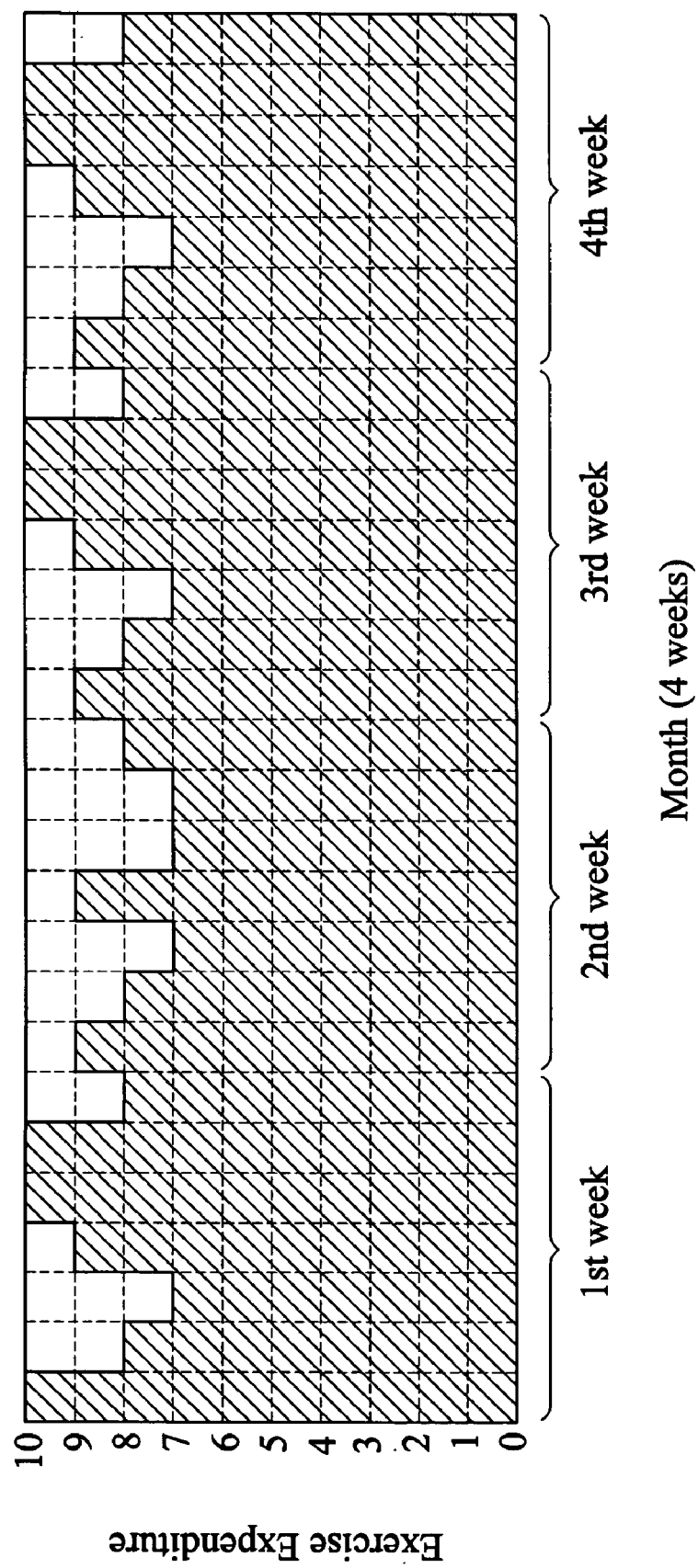
FIG. 4 shows the monthly graphic exercise expenditure distribution pattern of the user recorded by the device.

FIG. 4 shows the monthly graphic exercise expenditure distribution pattern of the user recorded by the device. The unit of the X-axis of the monthly exercise expenditure distribution pattern is week. The monthly exercise expenditure distribution pattern storage 81 stores the exercise expenditure that the user is taken in 4 weeks. In another embodiment, the exercise monitoring and recording device also comprises a yearly exercise expenditure distribution pattern for storing the exercise expenditure distribution pattern in one year.

Moreover, the exercise monitoring and recording device comprises a display mode selecting unit 9 which enables the user to select the type of exercise expenditure distribution pattern to be displayed. When the microprocessor 2 receives a selection signal s3 from the display mode selecting unit 9, the microprocessor 2 retrieves the daily, weekly or monthly exercise expenditure distribution pattern in accordance with the user's selection from the exercise expenditure distribution pattern storage 81, 82, 83 and sends it to the display unit 3 for displaying.

From the daily, weekly and monthly exercise expenditure distribution patterns of the daily, weekly and monthly expenditure distribution storage 81, 82, 83, the user can monitor his expenditure at any day, week or month. Besides, the user can use the expenditure data for further evaluation or statistics.

Figure 5:
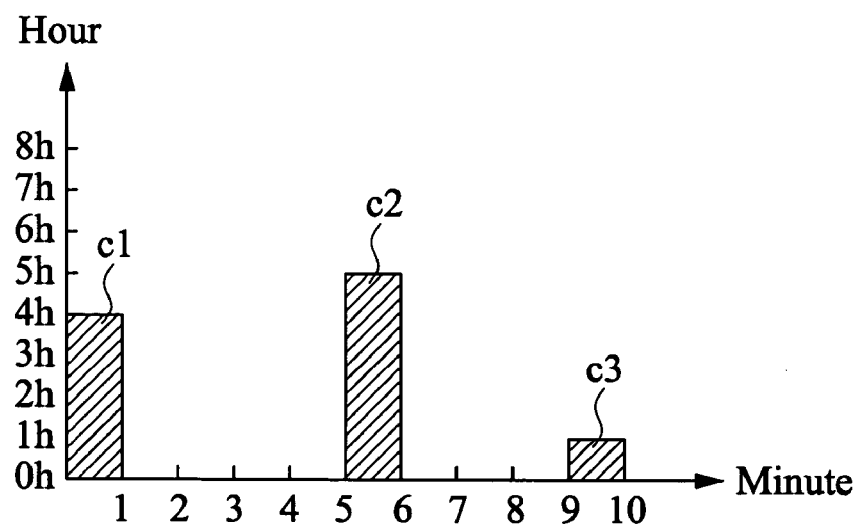
FIG. 5 is a bar chart showing the expenditure distribution of the user.

FIG. 5 is a bar chart showing the expenditure distribution of the user in walking, in which X-axis represents the interval of time that the user walks between rest, and Y-axis represents the accumulated time that the user walks for that interval of time. As shown, bar c1 represents the accumulated time that the user walk for an interval of 1 minute and it is equal to 4 hours, c2 represents the accumulated time that the user walk for an interval of 5~6 minutes and it is equal to 5 hours, and c3 represents the accumulated time that the user walk for an interval of 9~10 minutes and it is equal to 1 hour. Therefrom, the user can evaluate his exercise expenditure.

Figure 6:
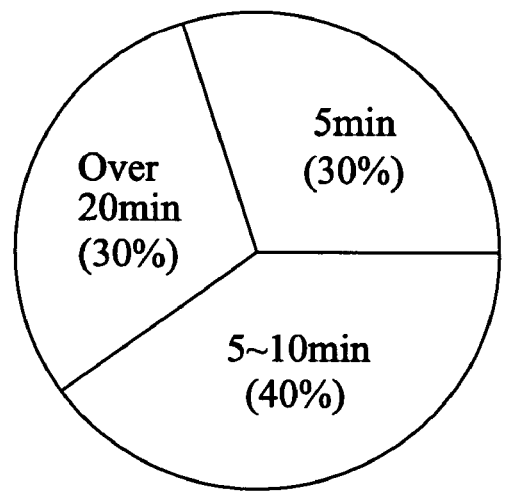
FIG. 6 is a pie chart showing the expenditure distribution of the user.

FIG. 6 is a pie chart showing the expenditure distribution of the user. According to the chart, the exercise expenditure that the user expends for an interval of less than 5 minutes accounts for 30% of the total exercise expenditure. The exercise expenditure that the user expends for an interval of 5~10 minutes accounts for 40% of the total exercise expenditure, and the exercise expenditure that the user expends for an interval of over 20 minutes accounts for 30% of the total exercise expenditure. Such an information is helpful for the user to make his exercise plan.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. An exercise monitoring and recording device for recording an exercise expenditure of a user and displaying graphic exercise expenditure distribution patterns, comprising:

a motion signal sensing circuit, which comprises a vibration sensor for detecting a series of motion signals of the user at exerciser;

a microprocessor, which receives the motion signals of the motion signal sensing circuit;

a time base signal unit, which provides a time base signal to the microprocessor;

a real time clock generating circuit, which provides a real time signal to the microprocessor; and at least one exercise expenditure distribution pattern storage, which is coupled to the microprocessor for storing the motion signals detected by the motion signal sensing circuit and generating a graphic exercise expenditure distribution pattern with reference to the real time signal provided by the real time clock generating circuit;

a display unit, which is coupled with the microprocessor for displaying the graphic exercise expenditure distribution pattern.

2. The exercise monitoring and recording device as claimed in claim 1, wherein the motion signal sensing circuit comprises a pedometer.

3. The exercise monitoring and recording device as claimed in claim 1, wherein the exercise expenditure distribution pattern storage comprises a daily exercise expenditure distribution pattern storage, which stores the daily exercise expenditure distribution pattern of the user.

4. The exercise monitoring and recording device as claimed in claim 1, wherein the exercise expenditure distribution pattern storage comprises a weekly exercise expenditure distribution pattern storage, which stores the weekly exercise expenditure distribution pattern of the user.

5. The exercise monitoring and recording device as claimed in claim 1, wherein the exercise expenditure distribution pattern storage comprises a monthly exercise expenditure distribution pattern storage, which stores the monthly exercise expenditure distribution pattern of the user.

6. The exercise monitoring and recording device as claimed in claim 1, wherein the exercise expenditure distribution pattern storage comprises:
- a daily exercise expenditure distribution pattern storage, which stores the daily exercise expenditure distribution pattern of the user;
- a weekly exercise expenditure distribution pattern storage, which stores the weekly exercise expenditure distribution pattern of the user; and
- a monthly exercise expenditure distribution pattern storage, which stores the monthly exercise expenditure distribution pattern of the user;

wherein when the daily exercise expenditure distribution pattern storage contains data for over 24 hours, the daily exercise expenditure distribution pattern storage sends a carry signal to the microprocessor which transfers the exercise expenditure distribution pattern of the first day of the daily exercise expenditure distribution pattern to the weekly exercise expenditure distribution pattern storage, constituting the first day pattern of the weekly exercise expenditure distribution pattern; and when the weekly exercise expenditure distribution pattern storage contains data for over 7 days, the weekly exercise expenditure distribution pattern storage sends a carry signal to the microprocessor which transfers the exercise expenditure distribution pattern of the first week of the weekly exercise expenditure distribution pattern to the monthly exercise expenditure distribution pattern storage, constituting the first week pattern of the monthly exercise expenditure distribution pattern.

7. The exercise monitoring and recording device as claimed in claim 6, wherein the exercise monitoring and recording device further comprises a display mode selecting unit connecting to the microprocessor, which generates a selection signal to the microprocessor to retrieve the daily, weekly or monthly exercise expenditure distribution pattern from the daily exercise expenditure distribution pattern storage, weekly exercise expenditure distribution pattern storage or monthly exercise expenditure distribution pattern storage for displaying at the displaying unit.

* * * * *